United States Patent [19]

Ikezaki et al.

[11] Patent Number: 4,490,392
[45] Date of Patent: Dec. 25, 1984

[54] BENZYLALCOHOL DERIVATIVE AND PROCESS FOR PREPARING

[75] Inventors: Muneyoshi Ikezaki, Ageo; Takeshi Kanno, Omiya; Hajime Iwai, Hasuda; Masanori Inamasu, Misato, all of Japan

[73] Assignee: Tanabe Seiyaku Co., Ltd., Osaka, Japan

[21] Appl. No.: 928,431

[22] Filed: Jul. 27, 1978

[30] Foreign Application Priority Data

Aug. 11, 1977 [JP] Japan .................................. 52/96748
Jan. 12, 1978 [JP] Japan .................................. 53/2557
Jan. 20, 1978 [JP] Japan .................................. 53/5533
Jan. 20, 1978 [JP] Japan .................................. 53/5534

[51] Int. Cl.$^3$ ...................... A01N 37/30; C07C 91/16
[52] U.S. Cl. .................................. 424/330; 424/316; 260/501.18; 549/443; 564/271; 564/304; 564/357; 564/358; 564/363; 564/375; 564/381
[58] Field of Search ...................... 260/570.6, 501.18; 424/330; 564/363, 304

[56] References Cited

U.S. PATENT DOCUMENTS

| 3,139,441 | 6/1964 | Biel .......................... 260/570.6 X |
| 3,250,803 | 5/1966 | Dijk .......................... 260/570.6 X |
| 3,253,034 | 5/1966 | McLoughlin .................... 260/570.6 |
| 3,976,695 | 8/1976 | Kaiser et al. .................. 260/570.6 |
| 4,011,319 | 3/1977 | Kaiser et al. .................. 424/244 |
| 4,032,575 | 6/1977 | Ikezaki et al. ................. 260/570.6 |
| 4,052,506 | 10/1977 | Kaiser et al. ................. 424/244 |

FOREIGN PATENT DOCUMENTS

| 48336 | 6/1911 | Fed. Rep. of Germany ... 260/570.6 |
| 894396 | 10/1953 | Fed. Rep. of Germany ... 260/570.6 |
| 2315934 | 1/1977 | France .......................... 424/244 |
| 789033 | 1/1958 | United Kingdom ............. 260/570.6 |

*Primary Examiner*—Robert V. Hines
*Attorney, Agent, or Firm*—Jordan B. Bierman

[57] ABSTRACT

A benzylalcohol derivative of the formula:

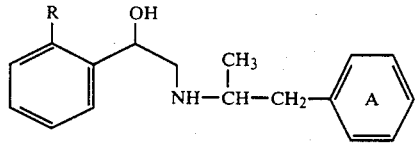

wherein R is hydroxy, benzyloxy, halogen or alkoxy having one to four carbon atoms, and Ring A is monomethoxyphenyl, dimethoxyphenyl, trimethoxyphenyl or 3,4-methylenedioxyphenyl, or a pharmaceutically acceptable acid addition salt thereof is prepared by reducing a compound of the formula:

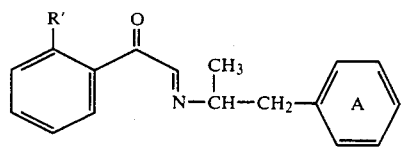

wherein R' is benzyloxy, halogen or alkoxy having one to four carbon atoms, and Ring A is the same as defined above, to give a compound of the formula:

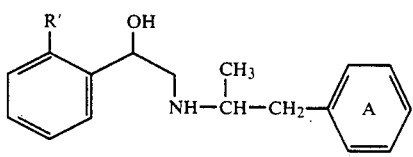

wherein R' and Ring A are the same as defined above, and when R' is benzyloxy, if required, further subjecting the compound [I'] to catalytic hydrogenation to give a compound of the formula:

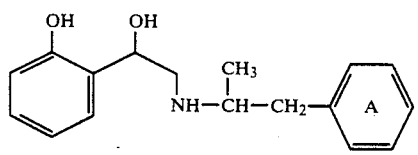

wherein Ring A is the same as defined above. The benzylalcohol derivative [I] is useful as an anti-diabetic agent.

35 Claims, No Drawings

BENZYLALCOHOL DERIVATIVE AND PROCESS FOR PREPARING

This invention relates to a novel benzylalcohol derivative and a process for preparing the same. More particularly, it relates to the α-[(α-methylphenethylamino)-methyl]benzylalcohol derivative of the formula:

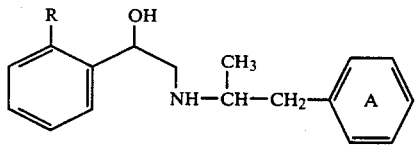

wherein R is hydroxy, benzyloxy, halogen or alkoxy having one to four carbon atoms, and Ring A is monomethoxyphenyl, dimethoxyphenyl, trimethoxyphenyl or 3,4-methylenedioxyphenyl, and pharmaceutically acceptable acid addition salts thereof.

It is known that α-[(α-methyl-3,4,5-trimethoxyphenethylamino)methyl]-3,4-dihydroxybenzylalcohol and α-[(α-methyl-3,4-methylenedioxyphenethylamino)methyl]-3,4-dihydroxybenzylalcohol are prepared by catalytic hydrogenation of the corresponding 3,4-dihydroxyacetophenone (U.S. Pat. Nos. 3,869,474 and 3,139,441). These compounds are useful as bronchodilators. It is also known that α-[(3,4-dimethoxyphenethylamino)methyl]-2-hydroxybenzylalcohol and α-[(3,4-dimethoxyphenethylamino)methyl]-2-methoxybenzylalcohol show a blood sugar-lowering activity and can be used as an anti-diabetic agent (U.S. Pat. No. 4,032,575 and German Offenlegungsschrift No. 2656088).

We have now found that the benzylalcohol derivative [I] can induce a remarkable decrease of blood sugar and is useful as an anti-diabetic agent. For example, when α-[(α-methyl-3,4-dimethoxyphenethylamino)methyl]-2-hydroxybenzylalcohol oxalate or α-[(α-methyl-3,4-dimethoxyphenethylamino)methyl]-2-methoxybenzylalcohol hydrochloride is administered orally to mice at a dose of 0.1 to one mg/kg immediately before subcutaneous injection of glucose (one g/kg), the increased blood sugar level is about 50% lower than that of a group of mice having been injected with glucose only. On the other hand, when examined under the same conditions as above, 100 mg/kg of Phenformin (Chemical name: 1-phenethyl-biguanide) or 6 mg/kg of α-[(3,4-dimethoxyphenethylamino)methyl]-2-hydroxybenzylalcohol hydrochloride are required to obtain almost the same blood sugar-lowering activity as in case of oral administration of said α-methyl-3,4-dimethoxyphenethylaminomethyl derivatives (Dose: 0.1–1.0 mg/kg) of the present invention.

The benzylalcohol derivative [I] includes a group of compounds which show a preventive effect upon the aggregation of blood platelets and are used in the treatment of thrombosis, while α-[(3,4-dimethoxyphenethylamino)methyl]-2-hydroxybenzylalcohol and α-[(3,4-dimethoxyphenethylamino)methyl]-2-methoxybenzylalcohol disclosed in U.S. Pat. No. 4,032,575 and German Offenlegungsschrift No. 2656088 show no substantial preventive effect upon the aggregation of blood platelets. Moreover, the benzylalcohol derivative [I] shows no substantial adrenergic β-action, such as cardiac contractile action (one of the side effects of an anti-diabetic agent), and the acute toxicity thereof is also low. For example, the maximum tolerance dose (M.T.D.) of α-[(α-methyl-3,4-dimethoxyphenethylamino)methyl]-2-hydroxybenzylalcohol oxalate, which is estimated 48 hours after intraperitoneal injection thereof to a group of four mice, is about 100 mg/kg.

In the above-mentioned formula [I], representative examples of the group R include hydroxy; benzyloxy; halogen such as chlorine and bromine; and alkoxy such as methoxy, ethoxy, propoxy and butoxy. On the other hand, representative examples of Ring A include monomethoxyphenyl such as 4-methoxyphenyl; dimethoxyphenyl such as 3,4-dimethoxyphenyl; trimethoxyphenyl such as 2,3,4-trimethoxyphenyl; and 3,4-methylenedioxyphenyl. Among those of the invention, a preferred subgenus includes the compound of formula [I] in which R is hydroxy, alkoxy of one to four carbon atoms, benzyloxy or chlorine, and Ring A is 4-methoxyphenyl, 3,4-dimethoxyphenyl, 2,3,4-trimethoxyphenyl or 3,4-methylenedioxyphenyl. Another preferred subgenus is the compound of the formula [I] in which R is hydroxy, methoxy, benzyloxy or chlorine and Ring A is 3,4-dimethoxyphenyl or 2,3,4-trimethoxyphenyl. An additional preferred subgenus is the compound of formula [I] in which R is hydroxy, methoxy, butoxy, benzyloxy or chlorine and Ring A is 3,4-dimethoxyphenyl. A further preferred subgenus of the invention is the compound of formula [I] in which R is hydroxy or methoxy and Ring A is 3,4-dimethoxyphenyl or 2,3,4-trimethoxyphenyl.

According to the present invention, the benzylalcohol derivative [I] can be prepared by the steps of:

(i) condensing a phenylglycol derivative of the formula:

wherein R' is benzyloxy, halogen or alkoxy having one to four carbon atoms; or a hydrate thereof with a phenethylamine derivative of the formula:

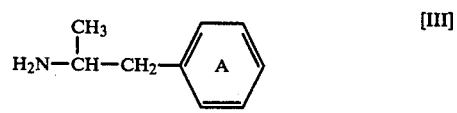

wherein Ring A is the same as defined above, to give an α-(α-methyl-phenethylimino)acetophenone derivative of the formula:

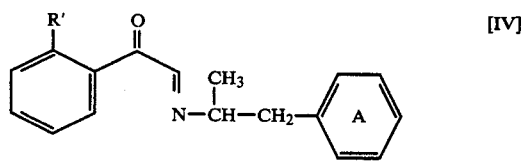

wherein R' and Ring A are the same as defined above, and (ii) reducing the acetophenone derivative [IV] to give a benzylalcohol derivative of the formula:

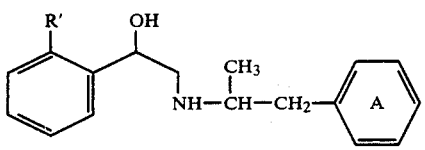

wherein R' and Ring A are the same as defined above. When R' is benzyloxy, said compound [I'] may be, if required, further subjected to catalytic hydrogenation to give a benzylalcohol derivative of the formula:

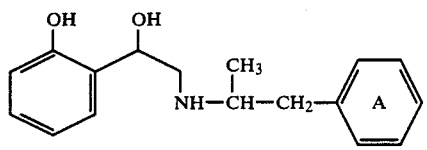

wherein Ring A is the same as defined above.

The starting compounds [II] and [III] are readily obtained. For example, compound [II] is obtained by oxidation of an acetophenone derivative of the formula:

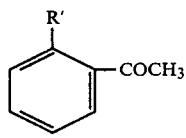

wherein R' is the same as defined above, with selenium dioxide according to a known method [cf. Chemical Abstracts, Vol. 66, 46399c(1967); ibid. Vol. 72, 89963y(1970)]. On the other hand, the starting compound [III] is obtained by reacting a benzaldehyde derivative of the formula:

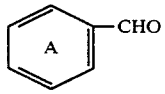

wherein Ring A is the same as defined above, with nitroethane to give a 1-phenyl-2-nitropropene derivative of the formula:

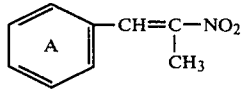

wherein Ring A is the same as defined above, and then reducing the 1-phenyl-2-nitropropene derivative with lithium aluminium hydride in a solvent [cf. Rec. trav. chem., 77, 273(1958)].

The condensation of the phenylglyoxal derivative [II] or a hydrate thereof with the phenethylamine derivative [III] can be readily accomplished. For example, the compound [IV] is prepared by admixing said starting compounds in the presence or absence of a catalyst in a solvent. It is preferred to carry out the reaction at a temperature of 0° to 50° C. Preferred examples of the reaction solvent include dimethylsulfoxide and lower alkanols (e.g., methanol, ethanol). p-Toluenesulfonic acid is suitable as the catalyst. The α-(α-methylphenethylimino)acetophenone derivative [IV] thus obtained may be used in the subsequent reaction without isolating it from the reaction solution.

The benzylalcohol derivative [I'] is prepared by treating the compound [IV] with a reducing agent in a solvent. Suitable examples of the reducing agent include an alkali metal borohydride (e.g., sodium borohydride, potassium borohydride, lithium borohydride), lithium aluminium hydride, diborane and aluminium hydride. Tetrahydrofuran, dioxane, lower alkanols (e.g., methanol, ethanol, propanol), a mixture of said lower alkanol and water, and the like are suitable as the reaction solvent. It is preferred to carry out the reaction at a temperature of −10° to 50° C.

The benzylalcohol derivative [I'] thus obtained usually exists in the form of a mixture of two diastereoisomers, and said mixture may be, if required, separated into each diastereoisomer. The separation of the diastereoisomers may be conducted by recrystallizing the mixture of said two diastereoisomers or salt thereof from a suitable solvent. The solvent employed in the separation procedure includes lower alkanols (e.g., methanol, ethanol, propanol, isopropanol), ethyl acetate, n-hexane, ethyl ether, isopropyl ether, acetone, benzene, water and a mixture thereof (e.g., a mixture of said lower alkanol and water, a mixture of said lower alkanol and acetone, a mixture of acetone and water, a mixture of benzene and n-hexane). Further, each diastereoisomer obtained above is still a mixture of the d- and l-enantiomers and may be, if required, resolved into each one of its optically active enantiomers. The optical resolution of said diastereoisomers may be carried out by reacting them with a resolving agent in a solvent to form the diastereoisomeric salts thereof, and separating said diastereoisomeric salts from each other by recrystallization. By said recrystallization, the least soluble diastereoisomeric salt is recovered as crystals from the reaction mixture and the more soluble diastereoisomeric salt remains soluble therein. It is preferred to carry out the recrystallization at −20° to 25° C. Derivatives of optically active tartaric acid (e.g., optically active enantiomers of dibenzoyltartaric acid, diacetyl-tartaric acid and monobenzoyl-tartaric acid), d-camphorsulfonic acid, d-α-bromocamphorsulfonic acid, L-(−)-malic acid, l-mandelic acid, quinic acid and optically active amino acids or their derivatives (e.g., optically active enantiomers of N-acetylphenylalanine, glutamic acid and N-carbobenzyloxyglutamic acid) may be used as the resolving agent. Examples of the solvent which are employed in this resolution procedure include water, lower alkanols (e.g., methanol, ethanol), ethyl acetate, chloroform, dimethylformamide or a mixture of these solvents.

The benzylalcohol derivative [I'] in which R' is benzyloxy may be, if required, further subjected to catalytic hydrogenation. This catalytic hydrogenation is carried out in the presence of a catalyst in a solvent and in a hydrogen atmosphere. Said benzylalcohol derivative employed in the catalytic hydrogenation may be either one of the two diastereoisomers, or a mixture thereof. Moreover, an optically active enantiomer of said benzylalcohol derivative may be employed for the catalytic hydrogenation. Preferred examples of the catalysts include platinum, platinum dioxide, palladium-black, palladium-carbon and the like. Lower alkanols (e.g., methanol, ethanol) are preferably employed as the solvent. It is preferred to carry out the reaction at a temperature of 20° to 50° C. It is also preferred to carry out the reaction under one to 5 atmospheres pressure. When the benzylalcohol derivative [I″] thus obtained is a mixture of two diastereoisomers, said mixture may be separated into each one of the diastereoisomers in the same manner as described hereinbefore.

The benzylalcohol derivative [I] of the present invention has two asymmetric carbon atoms and, as already described hereinbefore, can exist in the form of four stereoisomers. Said derivative can be used for pharmaceutical use in the form of either an optically active enantiomer, a mixture of d- and l-enantiomers (i.e., a racemic modification) or a mixture of four enantiomers (i.e., a diastereoisomeric mixture). The benzylalcohol derivative [I] can also be used for pharmaceutical use as either the free base or a salt thereof. The base and salt thereof are readily convertible from one to the other by conventional methods, as, for example, by treating a solution of the free base with an acid or by neutralizing a solution of the acid addition salt with an alkali metal salt (e.g., potassium carbonate). Examples of the pharmaceutically acceptable acid addition salts include inorganic acid addition salts such as hydrochloride, phosphate, nitrate and sulfate, and organic acid addition salts such as acetate, lactate, tartarate, fumarate, maleate, oxalate, succinate, methanesulfonate and benzoate. The benzylalcohol derivative [I] may be administered either orally or parenterally, and may be further used in conjunction or admixture with a pharmaceutical excipient which is suitable for oral or parenteral administration. The excipient selected should be the one which does not react with the benzylalcohol derivative [I]. Suitable excipients include, for example, gelatin, lactose, glucose, sodium chloride, starch, magnesium stearate, talcum, vegetable oil and benzylalcohol. The pharmaceutical preparation may be a solid dosage form such as pulvers, tablets and capsules, or a liquid dosage form such as a solution, an emulsion or a suspension. A daily dose of the benzylalcohol derivative [I] suitable for use as an anti-diabetic agent may be one $\mu$g to 10 mg, especially 5 $\mu$g to 5 mg, per kg of body weight.

Practical and presently-preferred embodiments of the present invention are illustratively shown in the following Examples.

EXAMPLE 1

(1) 2.26 g of 2-benzyloxyacetophenone are dissolved in 40 ml of dioxane, and a solution of 1.5 g of selenium dioxide in one ml of water is added thereto. The mixture is refluxed for 12 hours. After the reaction is completed, insoluble materials are removed by filtration, and the filtrate is condensed. The residue thus obtained is dissolved in ethyl acetate. The ethyl acetate solution is washed with water, an aqueous sodium bicarbonate solution and water, successively. Then, said solution is dried and evaporated to remove solvent. 2.3 g of 2-benzyloxyphenylglyoxal hydrate are obtained as a crude oil.

(2) 2.3 g of 2-benzyloxyphenylglyoxal hydrate (crude oil) are dissolved in 6 ml of dimethylsulfoxide, and 2 g of $\alpha$-methyl-3,4-dimethoxyphenethylamine are added thereto. The mixture is stirred at room temperature for 30 minutes, whereby a solution of $\alpha$-($\alpha$-methyl-3,4-dimethoxyphenethylimino)-2-benzyloxyacetophenone in dimethylsulfoxide is obtained.

(3) 12 ml of ethanol are added to the $\alpha$-($\alpha$-methyl-3,4-dimethoxyphenethylimino)-2-benzyloxyacetophenone solution obtained in paragraph (2). After ice-cooling, 0.5 g of sodium borohydride is added gradually to the solution, and the mixture is stirred at room temperature for 2 hours. The reaction mixture is evaporated to remove solvent. The residue thus obtained is dissolved in ethyl acetate. The ethyl acetate solution is washed with water, dried and evaporated to remove solvent, whereby $\alpha$-[($\alpha$-methyl-3,4-dimethoxyphenethylamino)-methyl]-2-benzyloxybenzylalcohol [the mixture of two diastereoisomers] is obtained as a crude oil. Said benzylalcohol [i.e., the mixture of two diastereoisomers] is dissolved in ethanol, and one g of oxalic acid is added thereto. The crystalline precipitates are collected by filtration (The filtrate is hereinafter referred to as "mother liquor"). 2 g of $\alpha$-[($\alpha$-methyl-3,4-dimethoxyphenethylamino)methyl]-2-benzyloxybenzylalcohol oxalate [the diastereoisomer of M.p. 152°–153° C. (decomp.)] are thereby obtained.

IR $\nu_{max}^{Nujol}$ (cm$^{-1}$): 3300, 3150, 1730, 1592.

Analysis calculated for $C_{26}H_{31}O_4N \cdot C_2H_2O_4$: C, 65.74; H, 6.50; N, 2.74. Found: C, 65.60; H, 6.53; N, 2.70.

Free base:
M.p. 104°–105° C. (recrystallized from ether)

On the other hand, the mother liquor is condensed. The residue is washed with ethyl ether and dissolved in ethanol. The ethanol solution is diluted with ethyl ether, whereby 0.7 g of $\alpha$-[($\alpha$-methyl-3,4-dimethoxyphenethylamino)methyl]-2-benzyloxybenzylalcohol ½ oxalate [the diastereoisomer of M.p. 186°–187° C. (decomp.)] is obtained.

IR $\nu_{max}^{Nujol}$ (cm$^{-1}$): 3420, 3240, 1595, 1520.

Analysis calculated for $C_{26}H_{31}O_4N \cdot \frac{1}{2}C_2H_2O_4$: C, 69.50; H, 6.91; N, 3.00. Found: C, 69.39; H, 6.77; N, 2.96.

Free base:
M.p. 84°–85° C. (recrystallized from ether)

(4-a) A mixture of one g of $\alpha$-[($\alpha$-methyl-3,4-dimethoxyphenethylamino)methyl]-2-benzyloxybenzylalcohol oxalate [the diastereoisomer of M.p. 152°–153° C. (decomp.)], 0.2 g of 10% palladium-carbon and 15 ml of 90% aqueous methanol is shaken at room temperature in hydrogen atmosphere under atmospheric pressure. After hydrogen uptake is completed, insoluble materials are removed by filtration, and the filtrate is condensed. The residue thus obtained is recrystallized from ethanol. 0.72 g of $\alpha$-[($\alpha$-methyl-3,4-dimethoxyphenethylamino)-methyl]-2-hydroxybenzylalcohol oxalate [the diastereoisomer of M.p. 155°–156° C. (decomp.)] is obtained.

IR $\nu_{max}^{Nujol}$ (cm$^{-1}$): 3570, 3460, 1700, 1602, 1592, 1508.

Analysis calculated for $C_{19}H_{25}O_4N \cdot C_2H_2O_4$: C, 59.85; H, 6.46; N, 3.32. Found: C, 60.17; H, 6.59; N, 3.33.

½ oxalate:
M.p. 190° C. (decomp.) (recrystallized from 80% aqueous ethanol)

½ sulfate:
M.p. 183° C. (recrystallized from ethanol)

Free base:
viscous oil

NMR (CDCl$_3$) ppm: 1.08 (d, 6 Hz, —CH—C$\underline{H}_3$, 3H) 2.4–3.3

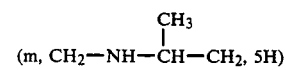

(m, CH$_2$—NH—CH—CH$_2$, 5H)

3.82 (s, OCH$_3 \times 2$, 6H) 4.78 (t, 5 Hz, C$\underline{H}$—OH, 1H) 5.68 (br. s, half height width 10 Hz, OH$\times 2,\overline{NH}$, 3H) 6.6–7.3 (m, aromatic H, 7H)

IR $\nu_{max}^{liq.}$ (cm$^{-1}$): 3450(br.), 3280, 1605(shoulder), 1585, 1510, 1450, 1420, 1260, 1240, 1140, 1030, 760.

(4-b) 0.2 g of α-[(α-methyl-3,4-dimethoxyphenethylamino)methyl]-2-benzyloxybenzylalcohol ½ oxalate [the diastereoisomer of M.p. 186°–187° C. (decomp.)] is treated in the same manner as described in paragraph (4-a). The crude product thus obtained is recrystallized from 80% aqueous ethanol, whereby 0.14 g of α-[(α-methyl-3,4-dimethoxyphenethylamino)methyl]-2-hydroxybenzylalcohol ½ oxalate [the diastereoisomer of M.p. 184°–185° C. (decomp.)] is obtained.

IR $\nu_{max}^{Nujol}$ (cm$^{-1}$): 3560, 3160, 1608, 1595, 1509.

Analysis calculated for $C_{19}H_{25}O_4N \cdot \frac{1}{2}C_2H_2O_4$: C, 63.81; H, 6.96; N, 3.72. Found: C, 63.62; H, 6.99; N, 3.67.

Free base:
Viscous oil
NMR (CDCl$_3$) ppm: 1.08 (d, 6 Hz, CH—C$\underline{H}_3$, 3H) 2.6–3.24

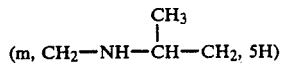

(m, CH$_2$—NH—CH—CH$_2$, 5H)

3.84 (s, OCH$_3$×2, 6H) 4.76 (t, 5 Hz, C$\underline{H}$—OH, 1H) 5.76 (br. s, half height width 14 Hz, OH×2, NH, 3H) 6.6–7.3 (m, aromatic H, 7H)

IR $\nu_{max}^{liq.}$ (cm$^{-1}$): 3450 (br.), 3280, 1605(shoulder), 1585, 1510, 1450, 1420, 1260, 1240, 1140, 1030, 760.

EXAMPLE 2

(1) 5 g of α-[(α-methyl-3,4-dimethoxyphenethylamino)methyl]-2-benzyloxybenzylalcohol [the diastereoisomer of M.p. 104°–105° C.] obtained in Example 1-(3) are dissolved in 30 ml of ethyl acetate, and 2.75 g of acetyl-D-phenylalanine are added thereto. The mixture is allowed to stand at 25° C. for 24 hours. The crystalline precipitates are collected by filtration, and washed with ethyl acetate, whereby 3.3 g of crystals are obtained. (The filtrate and the washing are combined, and the combined solution is referred to as "solution A") The crystals thus obtained are recrystallized from ethanol. The crystalline precipitates are collected by filtration, and washed with ethanol. (The filtrate and the washing are combined, and the combined solution is referred to as "solution B") 2.2 g of (+)-α-[(α-methyl-3,4-dimethoxyphenethylamino)methyl]-2-benzyloxybenzylalcohol acetyl-D-phenylalanine salt are thereby obtained [M.p. 131°–132° C., $[\alpha]_D^{25}$+13.5° (C=1.0, in methanol)]. The product thus obtained is dissolved in chloroform, and the solution is washed 10% aqueous potassium carbonate and water, successively. The solution is dried and evaporated to remove solvent. The crystals obtained are recrystallized from ethyl acetate, whereby 1.3 g of (+)-α-[α-methyl-3,4-dimethoxyphenethylamino)methyl]-2-benzyloxybenzylalcohol [d-enantiomer of M.p. 114°–115° C.] is obtained.

$[\alpha]_D^{25}$ +25.5° (C=1.0, in methanol)

On the other hand, solution A and solution B are combined, and the resulting solution is condensed. The residue thus obtained is dissolved in chloroform, and the solution is washed with 10% aqueous potassium carbonate and water, successively. Then, the solution is dried and evaporated to remove solvent, whereby about 3.6 g of crystals are obtained. The crystals are dissolved in 50 ml of ethyl acetate, and 1.9 g of acetyl-L-phenylalanine is added thereto. The solution is allowed to stand at 25° C. for 24 hours. The crystalline precipitates are collected by filtration, and recrystallized twice from ethanol. 2.44 g of (−)-α-[(α-methyl-3,4-dimethoxyphenethylamino)methyl]-2-benzyloxybenzylalcohol acetyl-L-phenylalanine salt are thereby obtained. M.p. 131°–132° C., $[\alpha]_D^{25}$ $-13.2°$ (C=1.0, in methanol) The product thus obtained is treated with 10% aqueous potassium carbonate in the same manner as above to convert it into its free base, and the free base is recrystallized from ethyl acetate. 1.5 g of (−)-α-[(α-methyl-3,4-dimethoxyphenethylamino)methyl]-2-benzyloxybenzylalcohol [l-enantiomer of M.p. 114°–115° C.] is thereby obtained.

$[\alpha]_D^{25}$ $-25.2°$ (C=1.0, in methanol)

(2-a) A mixture of 500 mg of (+)-α-[(α-methyl-3,4-dimethoxyphenethylamino)methyl]-2-benzyloxybenzylalcohol [d-enantiomer of M.p. 114°–115° C.], 55 mg of oxalic acid, 150 mg of 10% palladium-carbon and 10 ml of 90% aqueous methanol is shaken at room temperature in a hydrogen atmosphere under atmospheric pressure. After the hydrogen uptake is completed, insoluble materials are removed by filtration, and the filtrate is condensed. The residue thus obtained is recrystallized from ethanol, and dried at 80° C. under reduced pressure overnight. 377 mg of (+)-α-[(α-methyl-3,4-dimethoxyphenethylamino)methyl]-2-hydroxybenzylalcohol ½ oxalate [d-enantiomer of M.p. 173° C. (decomp.)] are thereby obtained.

$[\alpha]_D^{25}$ +25.5° (C=0.72, in methanol)

(2-b) A mixture of 1.2 g of (−)-α-[(α-methyl-3,4-dimethoxyphenethylamino)methyl]-2-benzyloxybenzylalcohol [l-enantiomer of M.p. 114°–115° C.], 130 mg of oxalic acid, 360 mg of 10% palladium-carbon and 20 ml of 90% aqueous methanol is treated in the same manner as described in paragraph (2-a). 950 mg of (−)-α-[(α-methyl-3,4-dimethoxyphenethylamino)methyl]-2-hydroxybenzylalcohol ½ oxalate [l-enantiomer of M.p. 173° C. (decomp.)] are thereby obtained.

$[\alpha]_D^{25}$ $-24.7°$ (C=0.77, in methanol)

EXAMPLE 3

(1) A mixture of 3 g of 2-benzyloxyacetophenone, 2 g of selenium dioxide, 15 ml of dioxane and 1.5 ml of water is treated in the same manner as described in Example 1-(1). 3.08 g of 2-benzyloxyphenylglyoxal hydrate are thereby obtained as a crude oil.

(2) 3.08 g of 2-benzyloxyphenylglyoxal hydrate (crude oil) are dissolved in 10 ml of dimethylsulfoxide, and 2.1 g of α-methyl-4-methoxyphenethylamine are added thereto. The mixture is stirred at room temperature for 45 minutes, whereby a solution of α-(α-methyl-4-methoxyphenethylimino)-2-benzyloxyacetophenone in dimethylsulfoxide is obtained.

(3) 20 ml of ethanol are added to the α-(α-methyl-4-methoxyphenethylimino)-2-benzyloxyacetophenone solution obtained in paragraph (2). After ice-cooling, 0.63 g of sodium borohydride is added gradually to the solution, and the mixture is stirred at room temperature for 2 hours. The reaction mixture is treated in the same manner as described in Example 1-(3), whereby α-[(α-methyl-4-methoxyphenethylamino)methyl]-2-benzyloxybenzylalcohol [the mixture of two diastereoisomers] is obtained as a crude oil. Said benzylalcohol [i.e., the mixture of two diastereoisomers] is treated with oxalic acid to convert it into its oxalate, and the oxalate is recrystallized from ethanol. The crystalline precipitates are collected by filtration (the filtrate is hereinafter referred to as "mother liquor"). 2.23 g of α-[(α-methyl-4-methoxyphenethylamino)methyl]-2-benzyloxybenzylalcohol oxalate [the diastereoisomer of M.p. 138°–139° C. (decomp.)] are thereby obtained.

IR $\nu_{max}^{Nujol}$ (cm$^{-1}$): 3300, 1720, 1615, 1510.

Analysis calculated for $C_{25}H_{29}O_3N \cdot C_2H_2O_4$: C, 67.34; H, 6.49; N, 2.91. Found: C, 67.45; H, 6.68; N, 2.78.

Free base:

M.p. 96.5°–97.5° C. (recrystallized from isopropyl ether)

On the other hand, the mother liquor is condensed. The residue is crystallized with ethyl acetate, and the crystalline mass is recrystallized from ethanol in the presence of 300 mg of oxalic acid, whereby 1.44 g of α-[(α-methyl-4-methoxyphenethylamino)methyl]-2-benzyloxybenzylalcohol oxalate [the diastereoisomer of M.p. 143°–144° C. (decomp.)] is obtained.

IR $\nu_{max}^{Nujol}$ (cm$^{-1}$): 3250(br.), 3030, 1710(br.), 1605, 1590, 1510.

Analysis calculated for $C_{25}H_{29}O_3N \cdot C_2H_2O_4$: C, 67.34; H, 6.49; N, 2.91. Found: C, 67.40; H, 6.60; N, 2.76.

Free base:

M.p. 95.5°–96.5° C. (recrystallized from isopropyl ether)

(4-a) A mixture of 1.5 g of α-[(α-methyl-4-methoxyphenethylamino)methyl]-2-benzyloxybenzylalcohol oxalate [the diastereoisomer of M.p. 138°–139° C. (decomp.)], 0.3 g of 10% palladium-carbon and 30 ml of 90% aqueous ethanol is treated in the same manner as described in Example 1-(4-a). The crude product is recrystallized from ethanol in the presence of 300 mg of oxalic acid, and crystalline precipitates are collected by filtration. 0.76 g of α-[(α-methyl-4-methoxyphenethylamino)methyl]-2-hydroxybenzylalcohol 3/2 oxalate [the diastereoisomer of M.p. 175°–176° C. (decomp.)] is thereby obtained.

IR $\nu_{max}^{Nujol}$ (cm$^{-1}$): 3270, 3180, 1710(br.), 1605, 1593.

Analysis calculated for $C_{18}H_{23}O_3N \cdot 3/2\ C_2H_2O_4$: C, 57.79; H, 6.01; N, 3.21. Found: C, 57.85; H, 6.14; N, 3.17.

Free base:

M.p. 132°–133° C. (recrystallized from a mixture of ethyl acetate and n-hexane)

IR $\nu_{max}^{Nujol}$ (cm$^{-1}$): 3290, 3180(br.), 1608, 1595, 1493, 1460, 1440, 1240, 1180, 1055, 1030 820, 770.

(4-b) A mixture of 0.7 g of α-[(α-methyl-4-methoxyphenethylamino)methyl]-2-benzyloxybenzylalcohol oxalate [the diastereoisomer of M.p. 143°–144° C. (decomp.)], 0.15 g of 10% palladium-carbon and 15 ml of 90% aqueous ethanol is treated in the same manner as described in Example 1-(4-a). The crude product thus obtained is recrystallized from ethanol. 0.48 g of α-[(α-methyl-4-methoxyphenethylamino)methyl]-2-hydroxybenzylalcohol oxalate [the diastereoisomer of M.p. 193°–194° C. (decomp.)] is thereby obtained.

IR $\nu_{max}^{Nujol}$ (cm$^{-1}$): 3270, 3050, 1790(br.), 1590.

Analysis calculated for $C_{18}H_{23}O_3N \cdot C_2H_2O_4$: C, 61.37; H, 6.44; N, 3.58. Found: C, 61.39; H, 6.47; N, 3.58.

Free base:

M.p. 100°–101° C. (recrystallized from a mixture of ethyl acetate and n-hexane)

IR $\nu_{max}^{Nujol}$ (cm$^{-1}$): 3300, 3200(br.), 1613, 1585, 1510, 1490, 1460, 1380, 1250, 1178, 1118, 1040, 885, 770, 760.

EXAMPLE 4

(1) A mixture of 3.9 g of 2,3,4-trimethoxybenzaldehyde, 3.7 g of nitroethane, 2.5 g of Amberlite IR-45 acetate and 200 ml of toluene is refluxed for 20 hours while removing the resultant water. After the reaction is completed, the reaction mixture is filtered, and the filtrate is evaporated to remove solvent. The residue thus obtained is recrystallized from a mixture of isopropyl ether and hexane. 4.3 g of 1-(2,3,4-trimethoxyphenyl)-2-nitropropene are thereby obtained as yellow cubes. M.p. 57°–58° C.

(2) 13 g of 1-(2,3,4-trimethoxyphenyl)-2-nitropropene are dissolved in 150 ml of tetrahydrofuran. The solution is added dropwise to a mixture of 5.9 g of lithium aluminium hydride and 100 ml of tetrahydrofuran under ice-cooling and under stirring. The mixture is refluxed for 3 hours under stirring. After ice-cooling, a mixture of 24 ml of tetrahydrofuran and 24 ml of water is added dropwise to the reaction mixture, and the aqueous solution is stirred at 20° C. for 2 hours. Then, insoluble materials are removed by filtration and washed with tetrahydrofuran. The filtrate and the washing are combined to form a solution. The combined solution is dried and evaporated to remove solvent. The residue thus obtained is distilled at a boiling point of 111°–113° C. under reduced pressure (2 mm Hg), whereby 8.5 g of α-methyl-2,3,4-trimethoxyphenethylamine are obtained as colorless oil.

(3) 8.8 g of 2-benzyloxyacetophenone are dissolved in 30 ml of dioxane, and a solution of 5.6 g of selenium dioxide in 3.5 ml of water is added thereto. The mixture is refluxed for 15 hours. After the reaction is completed, insoluble materials are removed by filtration, and the filtrate is evaporated to remove solvent. The residue thus obtained is extracted with benzene, and the benzene extract is washed with water, a saturated sodium bicarbonate solution, water and a saturated sodium chloride solution, successively. The extract is dried and evaporated to remove solvent. 10.3 g of 2-benzyloxyphenylglyoxal hydrate are thereby obtained as an orange yellow oil.

(4) 10.3 g of 2-benzyloxyphenylglyoxal hydrate are dissolved in 5 ml of dimethylsulfoxide. 7.6 g of α-methyl-2,3,4-trimethoxyphenethylamine are dissolved in 6 ml of dimethylsulfoxide, and the solution is added to the 2-benzyloxyphenylglyoxal solution under ice-cooling. The mixture is stirred at 20° C. for 2 hours, whereby a solution of α-(α-methyl-2,3,4-trimethoxyphenethylimino)-2-benzyloxyacetophenone in dimethylsulfoxide is obtained.

(5) 30 ml of ethanol are added to the α-(α-methyl-2,3,4-trimethoxyphenethylimino)-2-benzyloxyacetophenone solution obtained in paragraph (4). After ice-cooling, 2.2 g of sodium borohydride are added gradually to the solution, and the mixture is stirred at 20° C. for 2 hours. The reaction mixture is evaporated to remove solvent. The residue thus obtained is dissolved in ethyl acetate. The ethyl acetate solution is washed with water, 10% hydrochloric acid and water, successively. Then, the solution is dried and evaporated to remove solvent, whereby 18.2 g of yellow viscous oil are obtained. The oil is crystallized with a mixture of ether and benzene. 12.5 g of α-[(α-methyl-2,3,4-trimethoxyphenethylamino)methyl]-2-benzyloxybenzylalcohol hydrochloride [the mixture of two diastereoisomers] are thereby obtained. A mixture of benzene and ether is added to 10.5 g of said benzylalcohol hydrochloride [i.e., the mixture of two diastereoisomers] obtained above, and the crystalline precipitates are collected by filtration (the filtrate is hereinafter referred to as "mother liquor"). The precipitates are recrystallized from a mixture of benzene and ether (1:1), whereby 3.6 g of α-[(α-methyl-2,3,4-trimethoxyphenethylamino)methyl]-2-benzyloxybenzylalcohol hydrochloride [the diastereoisomer of M.p. 120°–121° C.] are obtained as colorless prisms.

IR $\nu_{max}^{Nujol}$ (cm$^{-1}$): 3320, 2800–2500, 1600, 1580, 1500.

Analysis calculated for $C_{27}H_{33}NO_5 \cdot HCl$: C, 66.45; H, 7.02; N, 2.87. Found: C, 66.69; H, 7.05; N, 2.86.

Free base:

M.p. 97°–98° C. (recrystallized from a mixture of isopropyl alcohol and isopropyl ether (1:1))

IR $\nu_{max}^{Nujol}$ (cm$^{-1}$): 3150(br.), 1600, 1580(shoulder), 1500.

NMR (CDCl$_3$) ppm: 1.0 (d, J=6 Hz, CHC$\underline{H}_3$, 3H) 2.3–3.3

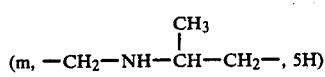

3.73, 3.76, 3.78 (s, OC$\underline{H}_3$, 9H) 4.99 (s, —OC$\underline{H}_2$—, 2H) 4.9–5.3 (m, C$\underline{H}$—OH, 1H) 7.26 (s, OCH$_2$C$_6$H$_5$, 5H) 6.3–7.7 (m, aromatic H, 6H)

On the other hand, the mother liquor is condensed, and the residue thus obtained is recrystallized from a mixture of benzene and ether (2:1). 2.7 g of α-[(α-methyl-2,3,4-trimethoxyphenethylamino)methyl]-2-benzyloxybenzylalcohol hydrochloride [the diasteroisomer of M.p. 135°–136° C.] are thereby obtained as colorless prisms.

IR $\nu_{max}^{Nujol}$ (cm$^{-1}$): 3330, 2800–2500, 1600, 1580, 1500.

Analysis calculated for $C_{27}H_{33}NO_5 \cdot HCl$: C, 66.45; H, 7.02; N, 2.87. Found: C, 66.47; H, 7.10; N, 2.88.

Free base:

M.p. 93°–94° C. (recrystallized from isopropyl alcohol) colorless needles

IR $\nu_{max}^{Nujol}$ (cm$^{-1}$): 3300, 3100(br.), 1600, 1580.

NMR (CDCl$_3$) ppm: 0.95 (d, 6 Hz, CHC$\underline{H}_3$, 3H) 2.3–3.2

3.81 (s, OC$\underline{H}_3$, 3H) 3.83 (s, OC$\underline{H}_3$, 3H) 5.06 (s, OC$\underline{H}_2$, 2H) 4.9–5.2 (m, C$\underline{H}$—OH, 1H) 6.4–7.7 (aromatic H, 11H)

Analysis calculated for $C_{27}H_{33}NO_5$: C, 71.81; H, 7.31; N, 3.10. Found: C, 71.82; H, 7.39; N, 2.98.

(6-a) A mixture of 1.5 g of α-[(α-methyl-2,3,4-trimethoxyphenethylamino)methyl]-2-benzyloxybenzylalcohol hydrochloride [the diastereoisomer of M.p. 120°–121° C.] obtained in paragraph (5), 500 mg of 10% palladium-carbon, 45 ml of ethanol and 5 ml of water is shaken at 20° C. for 2 hours in hydrogen atmosphere under atmospheric pressure. After hydrogen uptake is completed, insoluble materials are removed by filtration, and the filtrate is condensed. The residue thus obtained is recrystallized from a mixture of isopropylalcohol and isopropyl ether (1:2). 880 mg of α-[(α-methyl-2,3,4-trimethoxyphenethylamino)methyl]-2-hydroxybenzylalcohol hydrochloride [the diastereoisomer of M.p. 142°–143° C.] are thereby obtained as colorless cubes.

IR $\nu_{max}^{Nujol}$ (cm$^{-1}$): 3350(shoulder), 3300, 2800–2500, 1600, 1570, 1500.

Analysis calculated for $C_{20}H_{27}NO_5 \cdot HCl$: C, 60.37; H, 7.09; N, 3.52. Found: C, 60.42; H, 7.13; N, 3.54.

Free base:

Viscous oil

NMR (CDCl$_3$) ppm: 1.05 (d, 6 Hz, —CH—C$\underline{H}_3$, 3H) 2.36–3.24

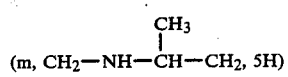

3.83 (s, OCH$_3$, 3H) 3.85 (s, OCH$_3\times$2, 6H) 4.80 (t, 5 Hz, CH—OH, 1H) 5.6 (br.s, half height width 8 Hz, OH$\times$2, NH, 3H) 6.52–7.26 (m, aromatic H, 6 Hz).

IR $\nu_{max}^{liq.}$ (cm$^{-1}$): 3300(br.), 1600, 1585, 1500, 1470, 1420, 1280, 1115, 760.

(6-b) A mixture of 1.0 g of α-[(α-methyl-2,3,4-trimethoxyphenethylamino)methyl]-2-benzyloxybenzylalcohol hydrochloride [the diastereoisomer of M.p. 135°–136° C.], 400 mg of 10% palladium-carbon, 45 ml of ethanol and 5 ml of water is treated in the same manner as described in paragraph (6-a). The crude product thus obtained is recrystallized from a mixture of isopropylalcohol and isopropyl ether (1:2). 590 mg of α-[(α-methyl-2,3,4-trimethoxyphenethylamino)methyl]-2-hydroxybenzylalcohol hydrochloride [the diastereoisomer of M.p. 145°–146° C.] are thereby obtained as colorless prisms.

IR $\nu_{max}^{Nujol}$ (cm$^{-1}$): 3380, 3220, 3060, 2800–2500, 1600, 1580, 1500.

Analysis calculated for $C_{20}H_{27}NO_5 \cdot HCl$: C, 60.37; H, 7.09; N, 3.52. Found: C, 60.48; H, 7.17; N, 3.50.

Free base:

Viscous oil

NMR (CDCl$_3$) ppm: 1.09 (d, 6 Hz, CH—C$\underline{H}_3$, 3H) 2.44–3.24

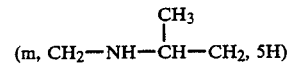

3.83 (s, OCH$_3$, 3H) 3.85 (s, OCH$_3$, 3H) 3.87 (s, OCH$_3$, 3H) 4.76 (t, 5 Hz, CH—OH, 1H) 5.60 (br.s, half height width 14 Hz, OH$\times$2, NH, 3H) 6.5–7.28 (m, aromatic H, 6H)

IR $\nu_{max}^{liq.}$ (cm$^{-1}$): 3300(br.), 1600, 1585, 1500, 1470, 1420, 1280, 1115, 760.

EXAMPLE 5

(1) 5 g of 2-methoxyacetophenone are dissolved in 30 ml of dioxane, and a solution of 4.8 g of selenium dioxide in 3 ml of water is added thereto. The mixture is refluxed for 6 hours. After the reaction is completed, insoluble materials are removed by filtration and the filtrate is condensed. The residue thus obtained is dissolved in ethyl acetate. The ethyl acetate solution is washed with water, an aqueous sodium bicarbonate solution and water, successively. Then, said solution is dried and evaporated to remove solvent. 4.9 g of 2-methoxyphenylglyoxal hydrate are thereby obtained as a crude oil.

(2) 4.9 g of 2-methoxyphenylglyoxal hydrate (crude oil) are dissolved in 15 ml of dimethylsulfoxide, and 5.25 g of α-methyl-3,4-dimethoxyphenethylamine are added thereto. The mixture is stirred at room temperature for 30 minutes, whereby a solution of α-(α-methyl-3,4-dimethoxyphenethylimino)-2-methoxyacetophenone in dimethylsulfoxide is obtained.

(3) 30 ml of ethanol are added to the α-(α-methyl-3,4-dimethoxyphenethylimino)-2-methoxyacetophenone solution obtained in paragraph (2). After ice-cooling, 1.53 g of sodium borohydride is added gradually to the solution, and the mixture is stirred at room temperature for 2 hours. The reaction mixture is treated in the same manner as described in Example 1-(3), whereby α-[(α-methyl-3,4-dimethoxyphenethylamino)methyl]-2-methoxybenzylalcohol [the mixture of two diastereoisomers] is obtained as a crude oil. Said benzylalcohol [i.e., the mixture of two diastereoisomers] is treated with oxalic acid to convert it into its oxalate, and the oxalate is recrystallized from 70% aqueous ethanol. The crystalline precipitates are collected by filtration (the filtrate is hereinafter referred to as "mother liquor"). 4.5 g of α-[(α-methyl-3,4-dimethoxyphenethylamino)methyl]-2-methoxybenzylalcohol ½ oxalate [the diastereoisomer of M.p. 199°-200° C. (decomp.)] are thereby obtained.

IR $\nu_{max}^{Nujol}$ (cm$^{-1}$): 3350, 1630, 1594, 1570, 1515.

Analysis calculated for $C_{20}H_{27}O_4N.\frac{1}{2}C_2H_2O_4$: C, 64.60; H, 7.23; N, 3.59. Found: C, 64.74; H, 7.32; N, 3.57.

Free base:

M.p. 95.5°-96.5° C. (recrystallized from isopropyl ether)

Hydrochloride:

M.p. 151°-153° C. (recrystallized from isopropanol)

On the other hand, the mother liquor is condensed, and the residue is neutralized with aqueous ammonia to convert it into its free base. The free base is purified by silica gel chromatography, and then recrystallized from ethanol. 1.9 g of α-[(α-methyl-3,4-dimethoxyphenethylamino)methyl]-2-methoxybenzylalcohol [the diastereoisomer of M.p. 125°-126° C.] is thereby obtained.

IR $\nu_{max}^{Nujol}$ (cm$^{-1}$): 3270, 3120(br.), 1595, 1585, 1515

Hydrochloride:

M.p. 165°-168° C. (recrystallized from isopropanol)

Analysis calculated for $C_{20}H_{27}O_4N.HCl$: C, 62.90; H, 7.39; N, 3.67; Cl, 9.28. Found: C, 63.01; H, 7.36; N, 3.66; Cl, 9.51.

EXAMPLE 6

(1) A mixture of 3 g of 2-methoxyacetophenone, 2.9 g of selenium dioxide, 20 ml of dioxane and 2 ml of water is treated in the same manner as described in Example 5-(1). 2.9 g of 2-methoxyphenylglyoxal hydrate are thereby obtained as a crude oil.

(2) 2.9 g of 2-methoxyphenylglyoxal hydrate (crude oil) are dissolved in 6 ml of dimethylsulfoxide, and 2 g of α-methyl-4-methoxyphenethylamine are added thereto. The mixture is treated in the same manner as described in Example 1-(2), whereby a solution of α-(α-methyl-4-methoxyphenethylimino)-2-methoxyacetophenone in dimethylsulfoxide is obtained.

(3) A mixture of the α-(α-methyl-4-methoxyphenethylimino)-2-methoxyacetophenone solution, 0.76 g of sodium borohydride and 12 ml of ethanol is treated in the same manner as described in Example 1-(3), whereby α-[(α-methyl-4-methoxyphenethylamino)methyl]-2-methoxybenzylalcohol [the mixture of two diastereoisomers] is obtained as a crude oil. Said benzylalcohol [i.e., the mixture of two diastereoisomers] is treated with ethanolic hydrogen chloride to convert it into its hydrochloride, and the hydrochloride is recrystallized from a mixture of ethanol and ether. The crystalline precipitates are collected by filtration (the filtrate is hereinafter referred to as "mother liquor"). 1.85 g of α-[(α-methyl-4-methoxyphenethylamino)methyl]-2-methoxybenzylalcohol hydrochloride [the diastereoisomer of M.p. 161°-163° C.] is thereby obtained.

IR $\nu_{max}^{Nujol}$ (cm$^{-1}$): 3350, 2600-2400, 1610, 1595, 1580.

Analysis calculated for $C_{19}H_{25}O_3N.HCl$: C, 64.85; H, 7.45; N, 3.98; Cl, 10.08. Found: C, 64.93; H, 7.58; N, 3.97; Cl, 10.07.

Free base:

M.p. 81.5°-82.5° C. (recrystallized from a mixture of isopropyl ether and n-hexane)

On the other hand, the mother liquor is condensed, and the residue is neutralized with 10% aqueous potassium carbonate to convert it into its free base. The free base is recrystallized from isopropyl ether, whereby 0.72 g of α-[(α-methyl-4-methoxyphenethylamino)methyl]-2-methoxybenzylalcohol [the diastereoisomer of M.p. 106°-107° C.] is obtained.

IR $\nu_{max}^{Nujol}$ (cm$^{-1}$): 3300, 3100(br.), 1610, 1598, 1580, 1510.

Analysis calculated for $C_{19}H_{25}O_3N$: C, 72.35; H, 7.99; N, 4.44. Found: C, 72.37; H, 7.99; N, 4.54.

Hydrochloride:

M.p. 143°-145° C. (recrystallized from a mixture of ethanol and ether).

EXAMPLE 7

(1) A mixture of 3.1 g of 2-n-butoxyacetophenone, 2.7 g of selenium dioxide, 30 ml of dioxane and 2 ml of water is treated in the same manner as described in Example 5-(1). 3.0 g of 2-n-butoxyphenylglyoxal hydrate are thereby obtained as a crude oil.

(2) 3.0 g of 2-n-butoxyphenylglyoxal hydrate (crude oil) are dissolved in 9 ml of dimethylsulfoxide, and 2.8 g of α-methyl-3,4-dimethoxyphenethylamine are added thereto. The mixture is stirred at room temperature for 30 minutes, whereby a solution of α-(α-methyl-3,4-dimethoxyphenylethylimino)-2-n-butoxyacetophenone in dimethylsulfoxide is obtained.

(3) A mixture of the α-(α-methyl-3,4-dimethoxyphenethylimino)-2-n-butoxyacetophenone solution obtained in paragraph (2), 0.8 g of sodium borohydride and 20 ml of ethanol is treated in the same manner as described in Example 1-(3), whereby α-[(α-methyl-3,4-dimethoxyphenethylamino)methyl]-2-n-butoxybenzylalcohol [the mixture of two diastereoisomers] is obtained as a crude oil. Said benzylalcohol [i.e., the mixture of two diastereoisomers] is treated with ethanolic hydrogen chloride to convert into its hydrochloride, and the hydrochloride is recrystallized from ethanol, whereby 4.0 g of α-[(α-methyl-3,4-dimethoxyphenethylamino)methyl]-2-n-butoxybenzylalcohol hydrochloride [the mixture of two diastereoisomers; M.p. 149°-152° C.] are obtained. Said benzylalcohol hydrochloride [i.e., the mixture of two diastereoisomers] is neutralized with 10% aqueous potassium carbonate to convert it into its free base, and ethanol is added to the free base. The crystalline precipitates are collected by filtration (the filtrate hereinafter referred to as "mother liquor"). 2.0 g of α-[(α-methyl-3,4-dimethoxyphenethylamino)methyl]-2-n-butoxybenzylalcohol [the diastereoisomer of M.p. 119°-121° C.] are thereby obtained.

IR $\nu_{max}^{Nujol}$ (cm$^{-1}$): 3290, 3130(br.), 1595, 1585, 1510.

Analysis calculated for $C_{23}H_{33}O_4N$: C, 71.29; H, 8.58; N, 3.61. Found: C, 71.20, H, 8.48; N, 3.55.

Hydrochloride:

M.p. 165°-166° C. (recrystallized from ethanol)

On the other hand, the mother liquor is condensed, and the oily residue is treated with ethanolic hydrogen chloride to convert into its hydrochloride. The hydrochloride is recrystallized from ethanol, whereby 1.2 g of α-[(α-methyl-3,4-dimethoxyphenethylamino)methyl]-2-n-butoxybenzylalcohol hydrochloride [the diastereoisomer of M.p. 168°–170° C.] is obtained.

IR $\nu_{max}^{Nujol}$ (cm$^{-1}$): 3340, 2500, 1600, 1590, 1580.

Analysis calculated for C$_{23}$H$_{33}$O$_4$N.HCl: C, 65.15; H, 8.08; N, 3.30. Found: C, 65.33; H, 8.01; N, 3.25.

EXAMPLE 8

(1) A mixture of 3 g of 2-chloroacetophenone, 2.74 g of selenium dioxide, 45 ml of dioxane and 2 ml of water is treated in the same manner as described in Example 5-(1). 3.0 g of 2-chlorophenylglyoxal hydrate are thereby obtained as a crude oil.

(2) 3.0 g of 2-chlorophenylglyoxal hydrate (crude oil) are dissolved in 9 ml of dimethylsulfoxide, and 2.5 g of α-methyl-4-methoxyphenylamine are added thereto. The mixture is treated in the same manner as described in Example 1-(2), whereby a solution of α-(α-methyl-4-methoxyphenethylimino)-2-chloroacetophenone in dimethylsulfoxide is obtained.

(3) A mixture of the α-(α-methyl-4-methoxyphenethylimino)-2-chloroacetophenone solution obtained in paragraph (2), one g of sodium borohydride and 18 ml of ethanol is treated in the same manner as described in Example 1-(3), whereby α-[(α-methyl-4-methoxyphenethylamino)methyl]-2-chlorobenzylalcohol [the mixture of two diastereoisomers] is obtained as a crude oil. Said benzylalcohol [i.e., the mixture of two diastereoisomers] is treated with ethanolic hydrogen chloride to convert it into its hydrochloride, and the hydrochloride is recrystallized from ethanol. The crystalline precipitates are collected by filtration (the filtrate is hereinafter referred to as "mother liquor"). 2.1 g of α-[(α-methyl-4-methoxyphenethylamino)methyl]-2-chlorobenzylalcohol hydrochloride [the diastereoisomer of M.p. 180°–181° C.] are thereby obtained.

IR $\nu_{max}^{Nujol}$ (cm$^{-1}$): 3150, 3100(shoulder), 2800–2400, 1610, 1510.

Analysis calculated for C$_{18}$H$_{22}$O$_2$NCl.HCl: C, 60.68; H, 6.51; N, 3.93; Cl, 19.90. Found: C, 60.42; H, 6.44; N, 3.81; Cl, 19.80.

Free base:

M.p. 87°–88° C. (recrystallized from a mixture of isopropyl ether and n-hexane).

On the other hand, the mother liquor is condensed, and the residue is neutralized with 10% aqueous potassium carbonate to convert it into its free base. The free base is purified by silica gel chromatography, and then treated with ethanolic hydrogen chloride to convert it into its hydrochloride. The hydrochloride is recrystallized from a mixture of ethanol and ether. 1.0 g of α-[(α-methyl-4-methoxyphenethylamino)methyl]-2-chlorobenzylalcohol hydrochloride [the diastereoisomer of M.p. 143°–144° C.] is thereby obtained.

IR $\nu_{max}^{Nujol}$ (cm$^{-1}$): 3260, 3070, 2700–2500, 1615, 1515.

Analysis calculated for C$_{18}$H$_{22}$O$_2$NCl.HCl: C, 60.68; H, 6.51; N, 3.93; Cl, 19.90. Found: C, 60.79; H, 6.55; N, 3.94; Cl, 20.01.

Free base:

M.p. 108°–109° C. (recrystallized from a mixture of benzene and n-hexane)

EXAMPLE 9

(1) A mixture of 5.1 g of 2-chloroacetophenone, 4.7 g of selenium dioxide, 70 ml of dioxane and 3.5 ml of water is treated in the same manner as described in Example 5-(1). 5.0 g of 2-chlorophenylglyoxal hydrate are thereby obtained as a crude oil.

(2) 5.0 g of 2-chlorophenylglyoxal hydrate (crude oil) are dissolved in 15 ml of dimethylsulfoxide, and 4.7 g of α-methyl-3,4-dimethoxyphenethylamine are added thereto. The mixture is treated in the same manner as described in Example 1-(2), whereby a solution of α-(α-methyl-3,4-dimethoxyphenethylimino)-2-chloroacetophenone in dimethylsulfoxide is obtained.

(3) A mixture of the α-[(α-methyl-3,4-dimethoxyphenethyl]imino)-2-chloroacetophenone solution obtained in paragraph (2), 1.38 g of sodium borohydride and 30 ml of ethanol is treated in the same manner as described in Example 1-(3), whereby α-[(α-methyl-3,4-dimethoxyphenethylamino)methyl]-2-chlorobenzylalcohol [the mixture of two diastereoisomer] is obtained as a brown oil. Said benzylalcohol [i.e., the mixture of two diastereoisomers] is treated with ethanolic hydrogen chloride to convert it into its hydrochloride, and the hydrochloride is recrystallized from ethanol. The crystalline precipitates are collected by filtration (the filtrate is hereinafter referred to as "mother liquor"). 2.98 g of α-[(α-methyl-3,4-dimethoxyphenethylamino)-methyl]-2-chlorobenzylalcohol hydrochloride [the diastereoisomer of M.p. 175°–176° C.] are thereby obtained.

IR $\nu_{max}^{Nujol}$ (cm$^{-1}$): 3220, 3150(shoulder), 2800–2600, 1605, 1595, 1570, 1550, 1505.

Analysis calculated for C$_{19}$H$_{24}$O$_3$NCl.HCl: C, 59.07; H, 6.52; N, 3.63; Cl, 18.36. Found: C, 59.18; H, 6.50; N, 3.67; Cl, 18.18.

Free base:

M.p. 105°–106° C. (recrystallized from isopropyl ether)

On the other hand, the mother liquor is condensed, and the residue is neutralized with 10% aqueous potassium carbonate to convert it into its free base. The free base is purified by silica gel chromatography, and then recrystallized from ethyl acetate. 1.3 g of α-[(α-methyl-3,4-dimethoxyphenethylamino)methyl]-2-chlorobenzylalcohol [the diastereoisomer of M.p. 113°–114° C.] is thereby obtained.

IR $\nu_{max}^{Nujol}$ (cm$^{-1}$): 3310, 3070, 1590, 1510.

Analysis calculated for C$_{19}$H$_{24}$O$_3$NCl: C, 65.23; H, 6.91; N, 4.00; Cl, 10.13. Found: C, 65.25; H, 6.88; N, 4.05; Cl, 10.29.

EXAMPLE 10

(1) A mixture of 4.5 g of 2-methoxyacetophenone, 4.33 g of selenium dioxide, 30 ml of dioxane and 3 ml of water is treated in the same manner as described in Example 5-(1). 5 g of 2-methoxyphenylglyoxal hydrate are thereby obtained as a crude oil.

(2) 5 g of 2-methoxyphenylglyoxal hydrate (crude oil) are dissolved in 15 ml of dimethylsulfoxide, and 4.83 g of α-methyl-3,4-methylenedioxyphenethylamine are added thereto. The mixture is treated in the same manner as described in Example 1-(2), whereby a solution of α-(α-methyl-3,4-methylenedioxyphenethylimino)-2-methoxyacetophenone in dimethylsulfoxide is obtained.

(3) A mixture of the α-(α-methyl-3,4-methylenedioxyphenethylimino)-2-methoxyacetophenone solution obtained in paragraph (2), 1.73 g of sodium borohydride and 30 ml of ethanol is treated in the same manner as described in Example 1-(3), whereby α-[(α-methyl-3,4-methylenedioxyphenethylamino)methyl]-2-methoxybenzylalcohol [the mixture of two diastereoisomers] is obtained as a crude oil. Said benzylalcohol [i.e., the mixture of two diastereoisomers] is treated with ethanolic hydrogen chloride to convert it into its hydrochloride, and the hydrochloride is recrystallized from an aqueous acetone. The crystalline precipitates are collected by filtration (the filtrate is hereinafter referred to as "mother liquor"). 5.4 g of α-[(α-methyl-3,4-methylenedioxyphenethylamino)methyl]-2-methoxybenzylalcohol hydrochloride [the diastereoisomer of M.p. 152°–153° C.] are thereby obtained.

IR $\nu_{max}^{Nujol}$ (cm$^{-1}$): 3320, 2800–2500, 1600, 1590.

Analysis calculated for $C_{19}H_{23}O_4N \cdot HCl$: C, 62.38; H, 6.61; N, 3.83. Found: C, 62.26; H, 6.80; N, 3.81.

Free base:

Viscous oil

IR $\nu_{max}^{liq.}$ (cm$^{-1}$): 3280(br.), 3070(br.), 1595, 1580, 1480, 1460, 1440, 1235(br.), 1020(br.), 920, 800, 750.

On the other hand, the mother liquor is condensed, and the residue is recrystallized from a mixture of ethanol and ether. 1.35 g of α-[(α-methyl-3,4-methylenedioxyphenethylamino)methyl]-2-methoxybenzylalcohol hydrochloride [the diastereoisomer of M.p. 173°–175° C.] is thereby obtained.

IR $\nu_{max}^{Nujol}$ (cm$^{-1}$): 3320, 2800–2350, 1600, 1585.

Analysis calculated for $C_{19}H_{23}O_4N \cdot HCl$: C, 62.38; H, 6.61; N, 3.83. Found: C, 62.39; H, 6.66; N, 3.78.

Free base:

M.p. 104°–105° C. (recrystallized from isopropyl ether)

IR $\nu_{max}^{Nujol}$ (cm$^{-1}$): 3270, 3110(br.), 1600, 1580, 1490, 1460, 1235, 1100, 1070, 1030, 940, 930, 920, 750.

EXAMPLE 11

(1) A mixture of 4.64 g of 2-chloroacetophenone, 4.33 g of selenium dioxide, 25 ml of dioxane and 3 ml of water is treated in the same manner as described in Example 5-(1). 5 g of 2-chlorophenylglyoxal hydrate are thereby obtained as a crude oil.

(2) 5 g of 2-chlorophenylglyoxal hydrate (crude oil) are dissolved in 15 ml of dimethylsulfoxide, and 4.83 g of α-methyl-3,4-methylenedioxyphenethylamine are added thereto. The mixture is treated in the same manner as described in Example 1-(2), whereby a solution of α-(α-methyl-3,4-methylenedioxyphenethylimino)-2-chloroacetophenone in dimethylsulfoxide is obtained.

(3) A mixture of the α-(α-methyl-3,4-methylenedioxyphenethylimino)-B 2-chloroacetophenone solution obtained in paragraph (2), 1.73 g of sodium borohydride and 30 ml of ethanol is treated in the same manner as described in Example 1-(3), whereby α-[(α-methyl-3,4-methylenedioxyphenethylamino)methyl]-2-chlorobenzylalcohol [the mixture of two diastereoisomers] is obtained as a crude oil. Said benzylalcohol [i.e., the mixture of two diastereoisomers] is treated with ethanolic hydrogen chloride to convert it into its hydrochloride, and the hydrochloride is recrystallized from methanol. The crystalline precipitates are collected by filtration (the filtrate is hereinafter referred to as "mother liquor"). 5.0 g of α-[(α-methyl-3,4-methylenedioxyphenethylamino)methyl]-2-chlorobenzylalcohol hydrochloride [the diastereoisomer of M.p. 202°–203° C. (decomp.)] are thereby obtained.

IR $\nu_{max}^{Nujol}$ (cm$^{-1}$): 3180, 3140(shoulder), 2800–2300, 1600, 1560.

Analysis calculated for $C_{18}H_{20}O_3NCl \cdot HCl$: C, 58.39; H, 5.72; N, 3.78. Found: C, 58.38; H, 5.79; N, 3.72.

Free base:

M.p. 93°–93.5° C. (recrystallized from isopropyl ether)

IR $\nu_{max}^{Nujol}$ (cm$^{-1}$): 3270, 3070, 1600, 1595(shoulder), 1570, 1440, 1380, 1340, 1250.

On the other hand, the mother liquor is condensed, and the residue is recrystallized from ethanol. 1.68 g of α[(α-methyl-3,4-methylenedioxyphenethylamino)methyl]-2-chlorobenzylalcohol hydrochloride [the diastereoisomer of M.p. 188°–189° C. (decomp.)] is thereby obtained.

IR $\nu_{max}^{Nujol}$ (cm$^{-1}$): 3450(shoulder), 3260, 2800–2400, 1600(shoulder), 1580.

Analysis calculated for $C_{18}H_{20}O_3NCl \cdot HCl$: C, 58.39; H, 5.72; N, 3.78. Found: C, 58.28; H, 5.91; N, 3.68.

Free base:

M.p. 103°–103.5° C. (recrystallized from isopropyl ether)

IR $\nu_{max}^{Nujol}$ (cm$^{-1}$): 3300, 3100(br.), 1630(shoulder), 1600, 1570, 1500(shoulder), 1490, 1460, 1440, 1380, 1340, 1255.

EXAMPLE 12

(1) A mixture of 5.0 g of 2-benzyloxyacetophenone, 3.2 g of selenium dioxide, 30 ml of dioxane and 2.5 ml of water is treated in the same manner as described in Example 1-(1). 5.2 g of 2-benzyloxyphenylglyoxal hydrate are thereby obtained as a crude oil.

(2) 5.2 g of 2-benzyloxyphenylglyoxal hydrate (crude oil) are dissolved in 15 ml of dimethylsulfoxide, and 3.54 g of α-methyl-3,4-methylenedioxyphenethylamine are added thereto. The mixture is treated in the same manner as described in Example 1-(2), whereby a solution of α-(α-methyl-3,4-methylenedioxyphenethylimino)-2-benzyloxyacetophenone in dimethylsulfoxide is obtained.

(3) A mixture of the α-(α-methyl-3,4-methylenedioxyphenethylimino)-2-benzyloxyacetophenone solution obtained in paragraph (2), 1.25 g of sodium borohydride and 30 ml of ethanol is treated in the same manner as described in Example 1-(3), whereby α-[(α-methyl-3,4-methylenedioxyphenethylamino)methyl]-2-benzyloxybenzylalcohol [the mixture of two diastereoisomers] is obtained as a caramel. Said benzylalcohol [i.e., the mixture of two diastereoisomers] is treated with ethanolic hydrogen chloride to convert it into its hydrochloride, and the hydrochloride is recrystallized from ethanol. The crystalline precipitates are collected by filtration (the filtrate is hereinafter referred to as "mother liquor"). 2.37 g of α-[(α-methyl-3,4-methylenedioxyphenethylamino)methyl]-2-benzyloxybenzylalcohol hydrochloride [the diastereoisomer of M.p. 185°–187° C.] are thereby obtained.

IR $\nu_{max}^{Nujol}$ (cm$^{-1}$): 3300, 2700–2300, 1595, 1580, 1490, 1450, 1375, 1255, 1240.

Analysis calculated for $C_{25}H_{27}O_4N \cdot HCl$: C, 67.94; H, 6.39; N, 3.17. Found: C, 67.96; H, 6.50; N, 3.14.

Free base:

M.p. 107.5°–108° C. (recrystallized from a mixture of ethyl acetate and n-hexane)

½ fumarate:

M.p. 170°–171° C. (decomp.) (recrystallized from a mixture of ethanol and ethyl acetate)

On the other hand, the mother liquor is condensed, and the residue is neutralized with 10% aqueous potassium carbonate to convert it into its free base. The free base is treated with fumaric acid to convert it into its fumarate, and the fumarate is recrystallized from methanol. 3.02 g of α-[(α-methyl-3,4-methylenedioxyphenethylamino)methyl]-2-benzyloxybenzylalcohol ½ fumarate [the diastereoisomer of M.p. 169°-170° C. (decomp.)] are thereby obtained.

IR $\nu_{max}^{Nujol}$ (cm$^{-1}$): 2700-2100, 1630, 1603, 1590, 1503, 1495, 1380, 1250.

Analysis calculated for $C_{25}H_{27}O_4N\cdot\frac{1}{2}C_4H_4O_4$: C, 69.95; H, 6.31; N, 3.02. Found: C, 69.98; H, 6.42; N, 2.98.

Free base:

M.p. 78°-79.5° C. (recrystallized from a mixture of ethyl acetate and n-hexane).

EXAMPLE 13

A mixture of 1.26 g of α-[(α-methyl-3,4-methylenedioxyphenethylamino)methyl]-2-benzyloxybenzylalcohol hydrochloride [the diastereoisomer of M.p. 185°-187° C.] obtained in Example 12-(3), 0.3 g of 10% palladium-carbon, 40 ml of ethanol and 2 ml of water is shaken at room temperature in a hydrogen atmosphere under atmospheric pressure. After the hydrogen uptake is completed, insoluble materials are removed by filtration, and the filtrate is condensed. The residue thus obtained is recrystallized from a mixture of ethanol and ether. 0.99 g of α-[(α-methyl-3,4-methylenedioxyphenethylamino)methyl]-2-hydroxybenzylalcohol hydrochloride [the diastereoisomer of M.p. 171°-172° C. (decomp.)] is thereby obtained.

IR $\nu_{max}^{Nujol}$ (cm$^{-1}$): 3490, 3400, 3280, 2750-2300, 1610, 1600, 1570.

½ oxalate:

M.p. 199°-200° C. (decomp.) (recrystallized from methanol)

Analysis calculated for $C_{18}H_{21}O_4N\cdot\frac{1}{2}C_2H_2O_4$: C, 63.32; H, 6.15; N, 3.89. Found: C, 63.29; H, 6.25; N, 3.93.

Free base:

M.p. 123°-124.5° C. (recrystallized from ethyl acetate)

IR $\nu_{max}^{Nujol}$ (cm$^{-1}$): 3300, 3100(br.), 1600, 1500, 1480, 1460, 1440, 1240, 1190, 1350, 820, 755.

EXAMPLE 14

A mixture of 140 mg of α-[(α-methyl-3,4-methylenedioxyphenethylamino)methyl]-2-benzyloxybenzylalcohol [the diastereoisomer of M.p. 78°-79.5° C.] obtained in Example 12-(3), 14 mg of oxalic acid, 100 mg of 10% palladium-carbon, 30 ml of ethanol and 2 ml of water is treated in the same manner as described in Example 2-(2-a). The crude product thus obtained is recrystallized from methanol, whereby 102 mg of α-[(α-methyl-3,4-methylenedioxyphenethylamino)methyl]-2-hydroxybenzylalcohol.½ oxalate [the diastereoisomer of M.p. 205°-206° C. (decomp.)] are obtained.

IR $\nu_{max}^{Nujol}$ (cm$^{-1}$): 3150, 2200(br.), 1640, 1580.

Analysis calculated for $C_{18}H_{21}O_4N\cdot\frac{1}{2}C_2H_2O_4$: C, 63.32; H, 6.15; N, 3.89. Found: C, 63.21; H, 6.21; N, 3.87.

Free base:

M.p. 105°-106° C. (recrystallized from a mixture of ethyl acetate and n-hexane)

IR $\nu_{max}^{Nujol}$ (cm$^{-1}$): 3290, 3220, 1583, 1483, 1440, 1243, 1190, 1035, 755.

What we claim is:

1. A compound of the formula:

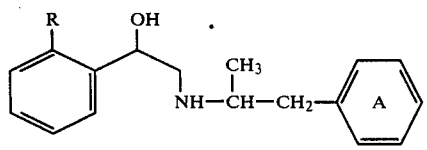

wherein R is hydroxy, benzyloxy, halogen or alkoxy of one to four carbon atoms, and Ring A is monomethoxyphenyl, dimethoxyphenyl, trimethoxyphenyl, or a pharmaceutically acceptable acid addition salt thereof.

2. The compound claimed in claim 1, in which Ring A is 4-methoxyphenyl, 3,4-dimethoxyphenyl, or 2,3,4-trimethoxyphenyl.

3. The compound claimed in claim 2, in which R is hydroxy, methoxy, n-butoxy, benzyloxy or chlorine.

4. The compound claimed in claim 2, in which R is hydroxy, methoxy, benzyloxy or chlorine.

5. The compound claimed in claim 2, in which R is hydroxy or methoxy.

6. The compound claimed in claim 2, in which R is hydroxy.

7. The compound claimed in claims 3,4,5 or 6, in which Ring A is 3,4-dimethoxyphenyl, or 2,3,4-trimethoxyphenyl.

8. The compound claimed in claims 3,4,5 or 6, in which Ring A is 4-methoxyphenyl, or 3,4-dimethoxyphenyl.

9. The compound claimed in claims 3,4,5 or 6, in which Ring A is 4-methoxyphenyl, 3,4-dimethoxyphenyl or 2,3,4-trimethoxyphenyl.

10. The compound claimed in claims 3,4,5 or 6, in which Ring A is 3,4-dimethoxyphenyl.

11. The compound claimed in claims 3,5 or 6, in which Ring A is 3,4-dimethoxyphenyl or 2,3,4-trimethoxyphenyl.

12. The compound claimed in claim 4, in which Ring A is 3,4-dimethoxyphenyl or 2,3,4-trimethoxyphenyl.

13. The compound claimed in claims 3,5 or 6, in which Ring A is 3,4-dimethoxyphenyl.

14. The compound claimed in claim 4, in which Ring A is 3,4-dimethoxyphenyl.

15. The compound claimed in claims 3,5 or 6, in which Ring A is 4-methoxyphenyl or 3,4-dimethoxyphenyl.

16. The compound claimed in claim 4, in which Ring A is 4-methoxyphenyl or 3,4-dimethoxyphenyl.

17. The compound of claim 10 which is α-[(α-methyl-3,4-dimethoxyphenethylamino)methyl]-2-hydroxybenzylalcohol or a pharmaceutically acceptable acid addition salt thereof.

18. The compound of claim 12 which is α-[(α-methyl-2,3,4-trimethoxyphenethylamino)methyl]-2-hydroxybenzylalcohol or a pharmaceutically acceptable acid addition salt thereof.

19. The compound of claim 12 which is α-[(α-methyl-3,4-dimethoxyphenethylamino)methyl]-2-methoxybenzylalcohol or a pharmaceutically acceptable acid addition salt thereof.

20. The compound of claim 12 which is α-[(α-methyl-3,4-dimethoxyphenethylamino)methyl]-2-benzyloxybenzylalcohol or a pharmaceutically acceptable acid addition salt thereof.

21. The compound of claim 12 which is α-[(α-methyl-3,4-dimethoxyphenethylamino)methyl]-2-chlorobenzylalcohol or a pharmaceutically acceptable acid addition salt thereof.

22. The compound of claim 16 which is α-[(α-methyl-4-methoxyphenethylamino)methyl]-2-benzyloxybenzylalcohol or a pharmaceutically acceptable acid addition salt thereof.

23. The compound of claim 17, which said α-[(α-methyl-3,4-dimethoxyphenethylamino)methyl]-2-hydroxybenzylalcohol in the form of free base is a diastereoisomer having the following nuclear magnetic resonance spectrum (in CDCl₃, ppm):

1.08 (d, 6 Hz, —CH—CH—C$\underline{H}$₃, 3H)

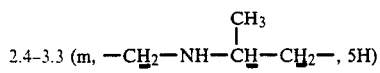

2.4–3.3 (m, —C$\underline{H}$₂—NH—C$\underline{H}$—C$\underline{H}$₂—, 5H)

3.82 (s, OCH₃×2, 6H) 4.78 (t, 5Hz, C$\underline{H}$—OH, 1H) 5.68 (br. s, half height width 10 Hz, $\overline{OH}$×2, NH, 3H) 6.6–7.3 (m, aromatic H, 7H).

24. The compound of claim 18, wherein said α-[(α-methyl-2,3,4-trimethoxyphenethylamino)methyl]-2-hydroxybenzylalcohol in the form of free base is a diastereoisomer having the following nuclear magnetic resonance spectrum (in CDCl₃, ppm):

1.05 ld, 6 Hz, —CH—C$\underline{H}$₃, 3H)

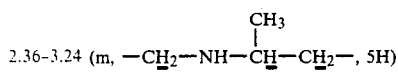

2.36–3.24 (m, —C$\underline{H}$₂—NH—C$\underline{H}$—C$\underline{H}$₂—, 5H)

3.83 (s, OCH₃, 3H) 3.85 (s, OCH₃×2, 6H) 4.80 (t, 5 Hz, C$\underline{H}$—OH, 1H) 5.6 (br. s, half height width 8 Hz, $\overline{OH}$×2, NH, 3H) 6.52–7.26 (m, aromatic H, 6 Hz).

25. The compound of claim 19, wherein said α-[(α-methyl-3,4-dimethoxyphenethylamino)methyl]-2-methoxybenzylalcohol in the form of free base is a diastereoisomer having a melting point of 95.5°–96.6° C.

26. The compound of claim 19, wherein said α-[(α-methyl-3,4-dimethoxyphenethylamino)methyl]-2-methoxybenzylalcohol in the form of free base is a diastereoisomer having a melting point of 125°–126° C.

27. The compound of claim 21, wherein said α-[(α-methyl-3,4-dimethoxyphenethylamino)methyl]-2-chlorobenzylalcohol in the form of free base is a diastereoisomer having a melting point of 105°–106° C.

28. The compound of claim 21, wherein said α-[(α-methyl-3,4-dimethoxyphenethylaminoethyl]-2-chlorobenzylalcohol in the form of free base is a diastereoisomer having a melting point of 113°–114° C.

29. Optically active laevorotatory enantiomer of the compound claimed in claim 23.

30. Optically active dextrorotatory enantiomer of the compound claimed in claim 23.

31. A pharmaceutical composition consisting essentially of a therapeutically effective amount of the compound claimed in claims 1, 2, 3, 4, 5 or 6 and a pharmaceutically acceptable excipient.

32. The composition of claim 31, wherein said therapeutic amount is one μg to 10 mg per kilogram of body weight per day.

33. The composition of claim 31, wherein said therapeutic amount is 5 μg to 5 mg per kilogram of body weight per day.

34. A method of decreasing blood sugar comprising administering to a warm blooded animal a therapeutically effective amount of the compounds claimed in claims 1, 2, 3, 4, 5, or 6.

35. A method of decreasing blood sugar comprising administering to a warm blooded animal the composition of claim 31.

* * * * *